(12) United States Patent
Proett et al.

(10) Patent No.: US 6,755,079 B1
(45) Date of Patent: Jun. 29, 2004

(54) METHOD AND APPARATUS FOR DETERMINING FLUID VISCOSITY

(75) Inventors: Mark A. Proett, Missouri City, TX (US); Michael T. Pelletier, Houston, TX (US); Wei Han, Missouri City, TX (US); Bruce H. Storm, Jr., Houston, TX (US); Roger L. Schultz, Aubrey, TX (US); Thomas E. Ritter, Katy, TX (US)

(73) Assignee: Halliburton Energy Services, Inc., Dallas, TX (US)

(*) Notice: Subject to any disclaimer, the term of this patent is extended or adjusted under 35 U.S.C. 154(b) by 0 days.

(21) Appl. No.: 09/536,840

(22) Filed: Mar. 27, 2000

(51) Int. Cl.[7] ............................. G01N 11/04; E21B 47/10
(52) U.S. Cl. ................................ 73/152.18; 73/54.04
(58) Field of Search .................... 73/952.18, 54.04, 73/54.09, 861.52; 175/40

(56) References Cited

U.S. PATENT DOCUMENTS

| | | | |
|---|---|---|---|
| 3,248,938 A | 5/1966 | Hill et al. | |
| 3,353,403 A * | 11/1967 | Fredric et al. | 73/54.09 |
| 3,371,527 A | 3/1968 | Moulin | |
| 3,468,158 A | 9/1969 | Chien | |
| 3,473,368 A * | 10/1969 | Wilbur | 73/54.04 |
| 3,663,477 A * | 5/1972 | George | 516/41 |
| 3,699,042 A * | 10/1972 | Billy et al. | 507/109 |
| 3,838,598 A * | 10/1974 | Tompkins | 73/861.52 |
| 3,885,429 A | 5/1975 | Megyeri et al. | |
| 4,641,535 A | 2/1987 | Malguarnera | |
| 4,726,219 A * | 2/1988 | Pearson et al. | 73/54.04 |
| 4,757,709 A | 7/1988 | Czernichow | |
| 6,119,730 A | 9/2000 | McMillan | |
| 6,176,323 B1 * | 1/2001 | Weirich et al. | 175/40 |

OTHER PUBLICATIONS

Search Report for International Application No.: PCT/US01/40373.

* cited by examiner

*Primary Examiner*—Hezron Williams
*Assistant Examiner*—Jay Politzer
(74) *Attorney, Agent, or Firm*—Konneker & Smith, P.C.

(57) ABSTRACT

A downhole tool and method for determining the viscosity of a reservoir fluid, the tool including a passage having entry, intermediate and exit regions, in which the reservoir fluid flowing through the passage will have a lower Reynolds number in the intermediate region as compared to the entry region, the tool also including differential pressure gauge for measuring the differential pressure across the intermediate region, and either a velocity controller or fluid velocity meter, for either setting or measuring the fluid velocity.

13 Claims, 11 Drawing Sheets

METHOD AND APPARATUS FOR DETERMINING FLUID VISCOSITY

BACKGROUND OF THE INVENTION

1. Field of the Invention

In one aspect, the present invention relates to apparatus and methods for fluid handling and characterization. In another aspect, the present invention relates apparatus and methods for changing the flow characteristics of a fluid, and to determining physical properties of the fluid. In even another aspect, the present invention relates to apparatus and methods for changing the Reynolds number of a flowing fluid stream, and to determining the viscosity of the fluid. In still another aspect, the present invention relates to methods and apparatus for determining the viscosity of a fluid in a subterranean environment. In yet another aspect, the present invention relates to a down hole tool for use in a well bore for determining the viscosity of a well bore fluid.

2. Description of the Related Art

In the exploration for hydrocarbons, it is generally necessary to obtain physical properties of the subterranean environment, especially physical properties of the reservoir fluids.

However, determination of the viscosity of a reservoir fluid is not a trivial matter. There is the complexity of determining the viscosity of reservoir fluids of a wide variety and range of rheological properties. Further adding to the complexity, is that the fluids typically encountered include mud, mud cake fragments, mud filtrate, in addition to formation fluids like oil, gas, water, and quite often these are immiscible fluids.

Thus, while there have been many attempts to accurately and conveniently determine the viscosity of a reservoir fluid in situ, there still exists the need in the art for apparatus and methods for determining such viscosity.

There also exists the need in the art for apparatus and methods for determining viscosity of reservoir fluids of a wide variety and range of Theological properties.

These and other needs in the art will become apparent to those of skill in the art upon review of this specification, its claims and drawings.

SUMMARY OF THE INVENTION

It is an object of the present invention to provide for apparatus and methods for determining such viscosity.

It is another object of the present invention to provide for apparatus and methods for determining viscosity of reservoir fluids of a wide variety and range of rheological properties.

These and other objects of the present invention will become apparent to those of skill in the art upon review of this specification, its claims and drawings.

According to one embodiment of the present invention, there is provided a down hole tool for processing a reservoir fluid. The tool generally includes a housing suitable for insertion into the well bore, with the housing having a passage for receiving the fluid. The passage has an entry region, an intermediate region, and an exit region, wherein for a fluid flowing through the passage, the fluid may have an entry region Reynolds number greater than the intermediate region Reynolds number. Alternatively, the entry and intermediate region geometries are selected so that for a given fluid having a given viscosity and a given Reynolds number, the calculated velocities for the entry region and for the intermediate region will be different. The tool further includes a sensor for either directly measuring or otherwise determining the differential pressure across the intermediate region. The tool also includes a flow meter for measuring the velocity of fluid passing through the intermediate region or capability to control the flow rate in a known manner. In a more specific embodiment, the tool further includes a computer processor for determining physical characteristics of the fluid from the differential pressure or velocity of the fluid.

According to another embodiment of the present invention, there is provided a tool for processing a reservoir fluid. The tool includes a housing suitable for insertion into the well bore, the housing includes a passage for the reservoir fluid, said passage having an entry region, an intermediate region, and an exit region. For fluid flowing through the passage, the fluid may have an entry region Reynolds number greater than the intermediate region Reynolds number. Alternatively, the entry and intermediate region geometries are selected so that for a given fluid having a given viscosity and a given Reynolds number, the calculated velocities for the entry region and for the intermediate region will be different. The tool also includes a force sensor, non-limiting examples of which include strain, load cell, hydraulic transfer, and the like, for determining the force exerted by the flowing fluid, and a flow meter for measuring the velocity of fluid passing through the intermediate region, or a flow controller for controlling the flow rate in a given manner. In a more detailed embodiment, the tool may also include a computer or micro processor for determining physical characteristics of the fluid from the differential pressure or velocity of the fluid.

According to even another embodiment of the present invention, there is provided a housing suitable for insertion into the well bore, the housing defining a passage therethrough for providing fluid communication with the reservoir fluid. The passage has an entry region, an intermediate region, and an exit region, wherein for a fluid flowing through the passage, the fluid will have an entry region Reynolds number greater than the intermediate region Reynolds number. The tool further includes pressure sensor for measuring the differential pressure across the intermediate region, and a flow controller for controlling the velocity of fluid passing through the intermediate region. In a further embodiment, the tool optionally includes a processor for determining the viscosity of the fluid.

According to yet another embodiment of the present invention, there is provided a method for processing a reservoir fluid in a subterranean well bore penetrating a reservoir. The method includes passing the reservoir fluid through a passage having an entry region, an intermediate region, and an exit region, wherein for the fluid flowing through the passage, the fluid may have an entry region Reynolds number greater than the intermediate region Reynolds number. The method also includes determining the differential pressure across the intermediate region. The method even also includes determining the velocity of fluid passing through the intermediate region. The method may optionally include determining the viscosity of the fluid from the velocity and differential pressure.

According to still another embodiment of the present invention, there is provided a method for processing a reservoir fluid in a subterranean well bore penetrating a reservoir. The method includes passing the reservoir fluid through a passage having an entry region, an intermediate region, and an exit region, wherein for the fluid flowing through the passage, the fluid may have an entry region Reynolds number greater than the intermediate region Reynolds number. The method further includes controlling the velocity of fluid passing through the intermediate region. The method also includes determining the differential pressure across the intermediate region. The method may optionally include determining the viscosity of the fluid.

BRIEF DESCRIPTION OF THE DRAWINGS

The aspects of the present invention will be set forth in greater detail herein and, in particular, by reference to the illustrative figures described below where like elements have common labels.

DETAILED DESCRIPTION OF THE INVENTION.

General Overview of Tool and Method

The method of the present invention for determining the viscosity of a reservoir fluid generally includes sampling a stream of the fluid wherein the stream is characterized by a first Reynolds number, reducing (by the cross-sectional geometry of the passage/and or by control of the fluid velocity) the Reynolds number of the stream to a second Reynolds number less than the first Reynolds number, and then determining the viscosity of the fluid.

Alternatively, the cross-sectional geometry of the passage is defined such that for a given fluid, of a given viscosity, at a given Reynolds number, the calculated velocity in the first upstream part of the passage is different, preferably less than, the calculated velocity in the second downstream part of the passage, to maintain the same Reynolds number.

Determination of the fluid viscosity requires knowledge of the fluid velocity through the passage, which may either be controlled to a desired velocity or may be measured.

The apparatus of the present invention will be described according to several non-limiting example embodiments in which the viscosity of reservoir fluids can be determined according to Poiseuille's Law in a downhole tool.

The apparatus and methods of the present invention will provide more accurate viscosity determinations if the fluid system exhibits laminar flow, classically defined as the flow regime for which the Reynolds number is less than about 2100. Of course, while viscosity may still be determined if the system exhibits turbulent flow (i.e., Reynolds number greater than about 2100), it is believed that the accuracy will decrease with increasing turbulent Reynolds number.

Thus, it is believed that the present invention will accurately operate on a flowing fluid steam having a Reynolds number of less than about 4000, preferably less than about 3000, more preferably less than about 2500, and even more preferably less than about 2100. Of course, while the flowing stream could have a Reynolds number of greater than 4000, accuracy is believed to be sacrificed.

In the practice of the present invention, differential pressure or net force, and known flow rate as described above are required to measure viscosity.

The apparatus of the present invention utilizes a laminar flow element, differential pressure element for measuring differential pressure or force across the laminar flow element, a fluid controller for accurate rate control and measurement of the fluid.

In the practice of the present invention, the differential pressure or force may be measured utilizing any suitable apparatus and methods, non-limiting examples of which include, but are not limited to, measurement of the net force on the laminar flow element by use of either a load cell, or a spring and position transducer, inserting the laminar flow element between two extremely sensitive pressure gauges, or between the sensors of a differential pressure gauge.

Figure 1:
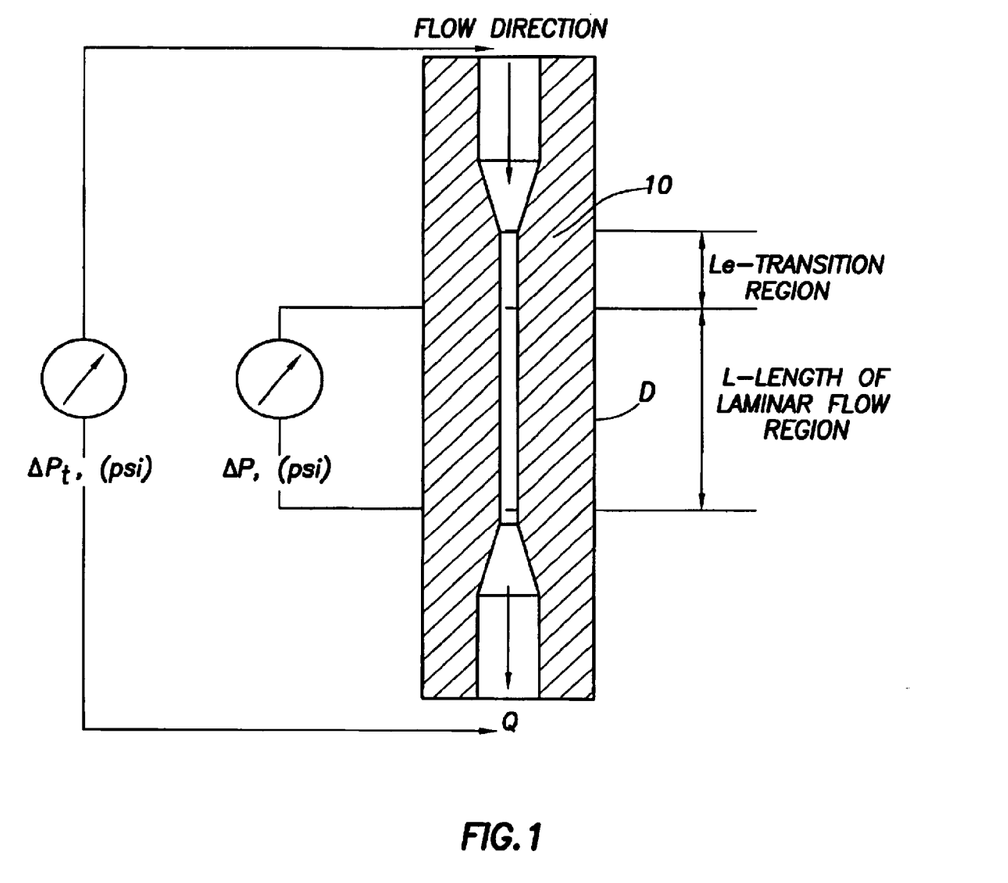
FIG. 1 is a schematic illustrating viscosity determination according to Poiseuille's Law.

In the practice of the present invention, fluid velocity may be controlled or measured by any suitable apparatus or method known to those of skill in the art, with the present invention not limited to any particular apparatus or method. general discussion of Poiseuille's Law Referring now to FIG. 1, Poiseuille's Law for a single capillary tube 10 can be used to determine the viscosity of a fluid in the laminar regime:

$$\mu = \frac{\Delta P D^4}{16 Q L} \tag{1}$$

wherein $\mu$=viscosity of fluid, $\Delta P$=differential pressure in laminar region, L=length between pressure points, D=diameter of the pipe, and Q=flow rate. Laminar flow is usually defined where the viscous pressure losses are linear with the flow rate, which is generally satisfied when the Reynolds number is less than about 2100. The Reynolds Number for a pipe is given by:

$$N_{re} = \frac{D V \rho}{\mu} \tag{2}$$

wherein $\rho$=density of fluid, $\mu$=Viscosity of fluid, V=average Velocity of fluid, D=Characteristic Length of system; for a pipe, it is the diameter, $D_L$=4*area of flow/wetted perimeter (hydraulic radius).

At the tube entrance the laminar flow regime may or may not be developed and a short distance may be required for this transition. This transition can be estimated using the following formula:

$$Le = \frac{D N_{re}}{32} \tag{3}$$

The pressure drop associated with this entrance transition is different from Eq. 1 and normally the total pressure is measured $\Delta P_t$ as shown in FIG. 1. There are also small pressure drops due to the pipe transitions so the total pressure measured is slightly higher than predicted from Poiseuille's Law. Assuming these additional pressure drops are small and are dominated by laminar flow then a system variable K can be used in Eq. 1 to characterize the total pressure drop as a function of viscosity and flow rate. It is obviously desirable to measure the differential pressure (or associated force) between two points which are maintained in laminar flow.

$$\mu = K \frac{\Delta P_t}{Q} \quad (4)$$

It is possible to extend the viscosity measurement using different cross-sectional geometries with a characteristic hydraulic length or diameter that maintains laminar flow. The hydraulic diameter may be directly calculated from the geometry of the system, or it may be measured by flowing a system of known viscosity at increasing rates until $\Delta p$ versus Q is no longer linear.

Extension of flow in a capillary tube to a laminar flow element desires the same cross sectional flow area, set by other sections of the tool, be maintained in the laminar flow element. This places stringent requirements on the sensitivity of the pressure measurement system, especially at low flow rates.

Laminar flow can be verified using Eq. 2 but the fluid density must be estimated or measured independently. Another approach to verify laminar flow is to plot viscosity (as returned by the sensor) vs. flow rate. The relationship will be linear if the flow regime is laminar. Transition to turbulent flow would be characterized by the viscosity being proportional to one over the square of the flow rate or, $$\mu = F \frac{\Delta P_t}{Q^2} \quad (5)$$

where F is the friction coefficient. The friction coefficient depends on the Reynolds Number and is linear over a limited range.

Figure 2:
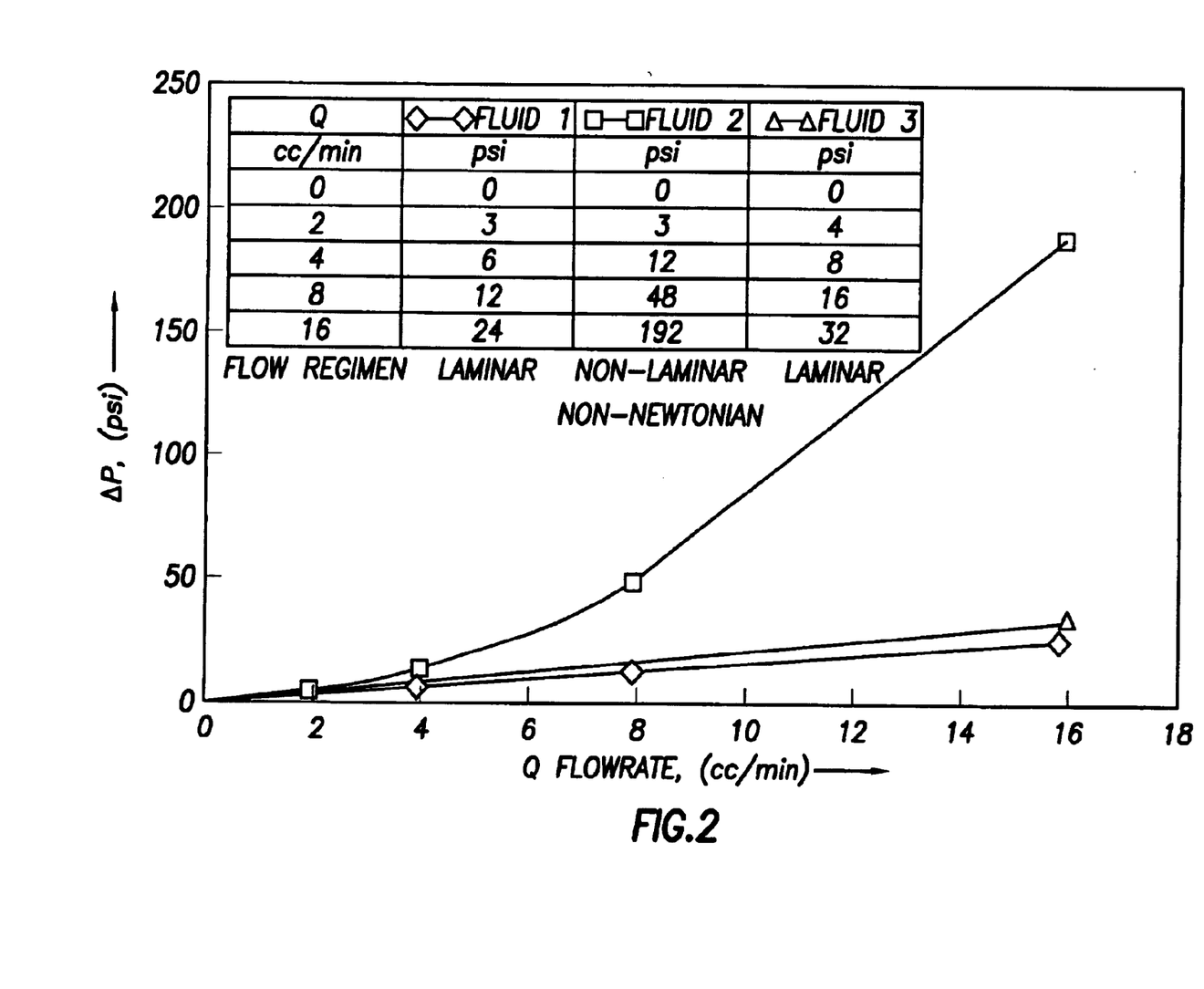
FIG. 2 is a graph showing for fluids 1 and 2 the display behavior characteristic of Newtonian fluids in laminar flow.

If the fluid is Newtonian, a graph of differential pressure ($\Delta P$) versus flow rate (Q) will be represented as a curve passing through the origin. If the curve is well described as a line, the system is in laminar flow and the slope of the line is proportional to the viscosity of the fluid. In FIG. 2, fluids 1 and 3 display behavior characteristic of Newtonian fluids in laminar flow. Fluid 2 deviates from this behavior; being both non-Newtonian and in turbulent flow.

Non-plugging Self-cleaning Embodiment

Figure 3:
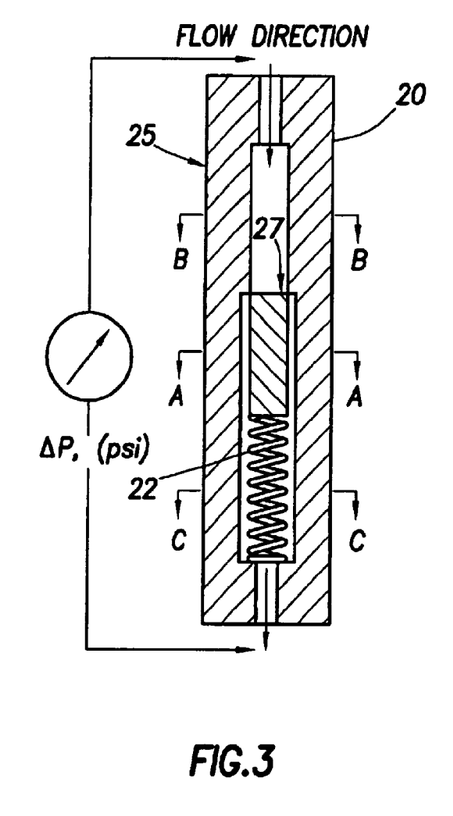
FIG. 3 is shown a schematic of one embodiment of the apparatus of the present invention, showing a spring 22 that is biasing a laminar flow cell 20 against stop 25.
Figure 3A:
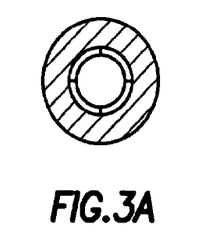
Figure 3B:
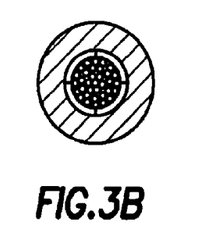
Figure 3C:
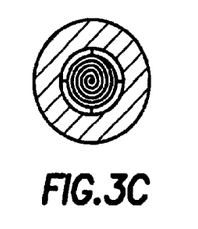
Figure 3D:
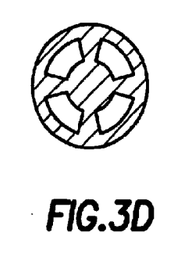
Figure 3E:
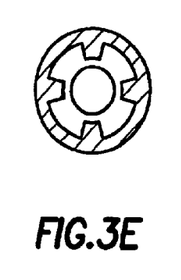

Referring now to FIG. 3, there is shown a schematic of one embodiment of the apparatus of the present invention, a spring 22 that is biasing a laminar flow cell 20 against stop 25, so that if the pressure differential exceeded a maximum limit, the laminar element 27 would be forced downward to relieve the plugging. When element 27 is forced down, the pressure reading would indicate plugging and an invalid result. Also, as pressure is increased across flow cell 20, the effective length of the annular volume around the cylindrical element 27 is reduced in length, adding dynamic range to the measurement.

It is believed that a number of alternative geometries find utility in the present invention, provided that the Reynolds number is effected, preferably reduced. Non-limiting examples of geometries include regular and irregular n sided geometric shapes wherein n ranges from 3 to about 50, and further includes geometries having linear and or curvalinear sides. Specific non-limiting examples include cylindrical, elongated tapered, and spiral members.

If there is no initial preload on the spring, or the viscous drag is larger than the initial preload, the cylinder will move changing the active length of the tube.

$$\Delta L = Li - L = f/k \quad (6)$$

wherein, $\Delta L$=change in length, Li=initial static length, f=viscous drag force, and k=spring constant.

The viscous drag force on the element is directly proportional to the pressure drop. Therefore, using system constants $C_1$ and $C_2$ the viscosity can be estimated using Eqs. 1 and 6:

$$f = C_1 \Delta P = C_2 \mu Q(Li - f/k) = C_2 \mu Q(Li - C_1 \Delta P/k) \quad (7)$$

Now, solving for viscosity, a modified form of equation 4 is obtained that includes the spring constant.

$$\mu = \frac{C_1}{C_2 L_i} \frac{\Delta P}{Q} \left( \frac{1}{1 - C_1 \Delta P/(kL_i)} \right) = K \frac{\Delta P}{Q} \left( \frac{1}{1 - C_1 \Delta P/(kL_i)} \right) \quad (8)$$

Solving for $\Delta P$ in Eq. 8 shows how the spring reduces $\Delta P$ required as the flow rate or viscosity is increased.

$$\Delta P = \frac{\mu Q}{K + \mu Q C_1/(kL_i)} \quad (9)$$

Reducing the pressure differential required reduces the load on the pump used to move the fluid which extends the range of measurement. While the relationship is not quite linear it can be characterized with two system constants K and $C_1$.

Bidirectional Non-plugging Self Cleaning Embodiment

Figure 4:
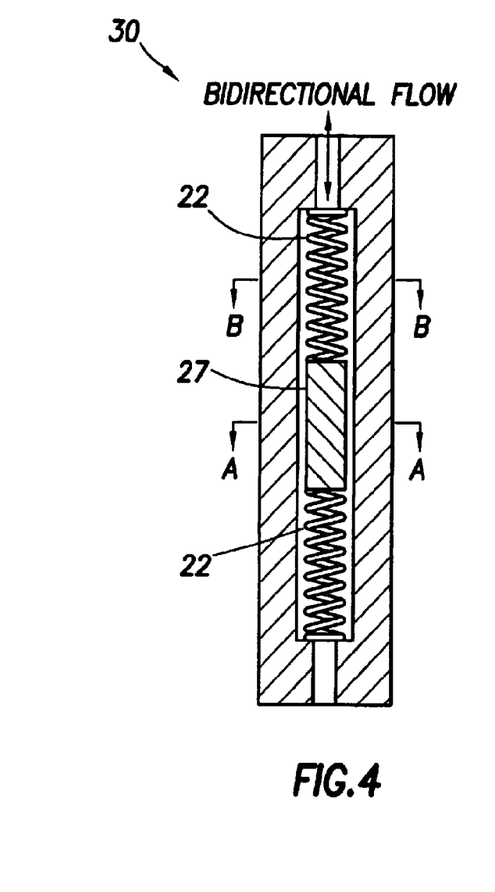
FIG. 4 is an illustration of bidirectional non-plugging self cleaning embodiment 30 of the present invention, having springs 22, and flow element 27.
Figure 4A:
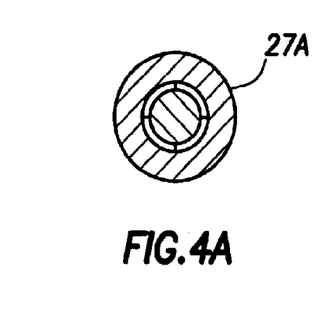
FIGS. 4A, 4B, and 4c, are illustrations of optional replacements for flow element 27, showing respectively, solid cylinder 27A, small cylinder 27B, and spiral cylinder 27C, at A—A of FIG. 4.
Figure 4B:
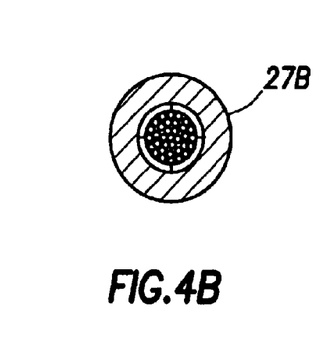
Figure 4C:
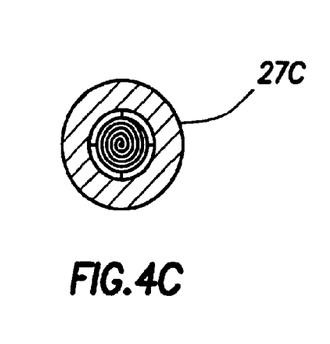
Figure 4D:
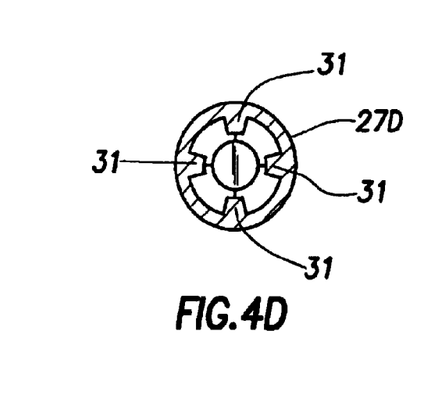
FIG. 4D is a top view of bidirectional non-plugging self cleaning embodiment 30, showing stops 31, at B—B of FIG. 4.

Referring now to FIG. 4, there is shown an example of a bidirectional non-plugging self cleaning embodiment 30 of the present invention, having springs 22, and flow element 27. FIGS. 4A, 4B, and 4c, are illustrations of optional replacements for flow element 27, showing respectively, solid cylinder 27A, small cylinder 27B, and spiral cylinder 27C.

To reduce the inner element's diameter, it could be composed of two or more concentric cylinders, each having the characteristic laminar flow spacing, (which is the embodiment shown is a non-limiting ~0.03 inches) with each cylinder supported by its own spring. Alternatively, an assembly of small hypodermic sized cylinders (which in the embodiment shown is about 0.03 inch ID) could be mounted in the inner cylinder. As a non-limiting alternative, a spiral shaped element, with the characteristic annular spacing may be utilized. These last two options would not be entirely self-cleaning, however, the design could be made symmetrical, so that bi-directional flow can be accommodated, as shown in FIG. 4. This enhances the capability to clean the element in the event of plugging.

Tapered Self-cleaning Embodiment

Figure 5:
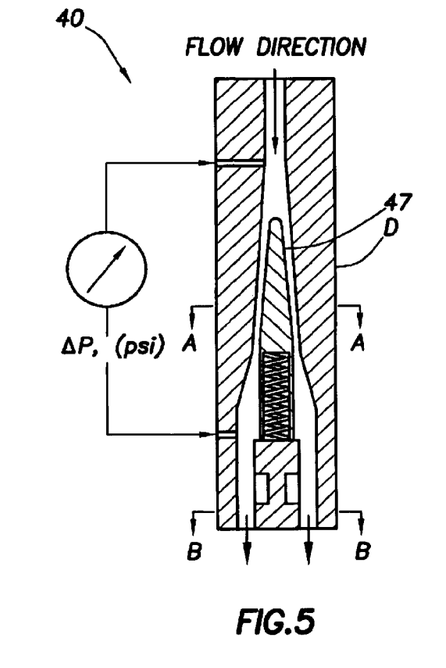
FIG. 5 is an illustration of tapered self-cleaning embodiment 40 of the present invention, in which the spring-loaded laminar flow element 47 can be tapered (cone shaped) as shown.
Figure 5A:
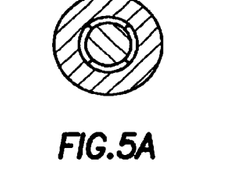
Figure 5B:
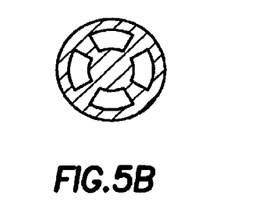

Referring now to FIG. 5, there is shown a non-limiting example of the tapered self-cleaning embodiment 40 of the present invention, in which the spring-loaded laminar flow element 47 can be tapered (cone shaped as shown). This improves the self-cleaning feature and further extends the dynamic range of the measurement. Now the characteristic hydraulic radius $D_L$ is increased as the spring is compressed opening the cone and cup spacing with a $\theta$ taper angle.

$$\Delta D = D - D_i = f \cdot \sin(\theta)/k \quad (10)$$

Therefore, using system constants $C_1$ and $C_2$ the viscosity can be estimated using Eqs. 1 and 6 and allowing D to vary.

$$f = C_1 \Delta P = \frac{C_2 \mu Q}{(D_i + \Delta D)^4} = \frac{C_2 \mu Q}{(D_i + (C_1 \Delta P)\sin(\theta)/k)^4} \quad (11)$$

Now solving for viscosity a modified form of equation 4 is obtained that includes the spring constant and cone angle.

$$\mu = K \frac{\Delta P}{Q}\left(1 + \frac{C_1 \Delta P \sin(\theta)}{D_i k}\right)^4 \quad (12)$$

Notice that smaller changes in pressure are required for a viscosity change than in Eq. 8 further extending the range of measurement for a given pressure differential.

Equations 7 and 11 demonstrate that a force or displacement measurement can be used to determine viscosity. Thus, if the force can be measured directly on the cone or cylinder elements, or on the housing, the viscosity can be determined directly when a spring is not used. If a spring is used the displacement can be determined from the spring rate and the measured force, and then the viscosity may be calculated. Conversely if the displacement of the cone or cylinder can be measured then the force can be estimated from the spring rate, and viscosity subsequently determined. Both methods eliminate the need for a pressure transducer (see FIG. 5), that is, by measuring pressure rather than force.

Density and Viscosity Determination

Figure 16A:
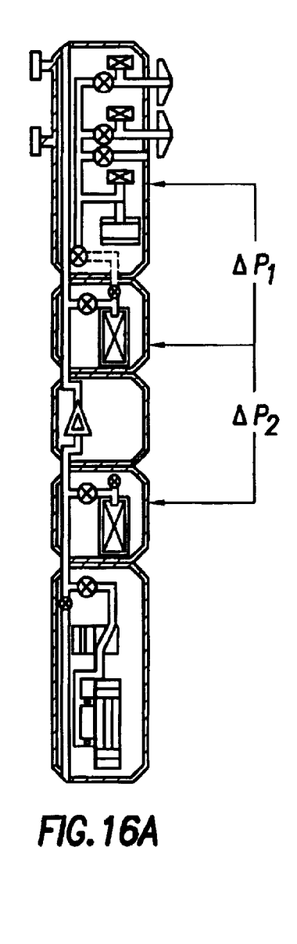
FIGS. 16A, 16B, and 16C show the determination of both density and viscosity.
Figure 16B:
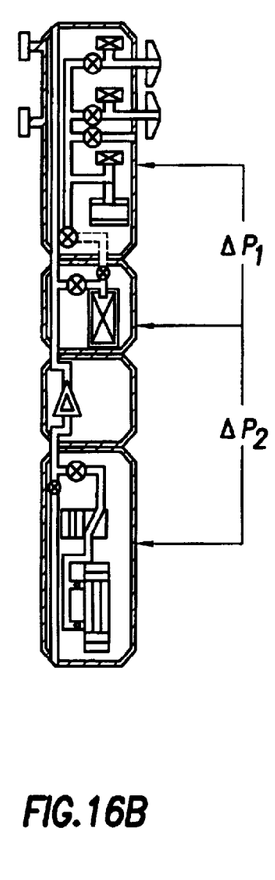
Figure 16C:
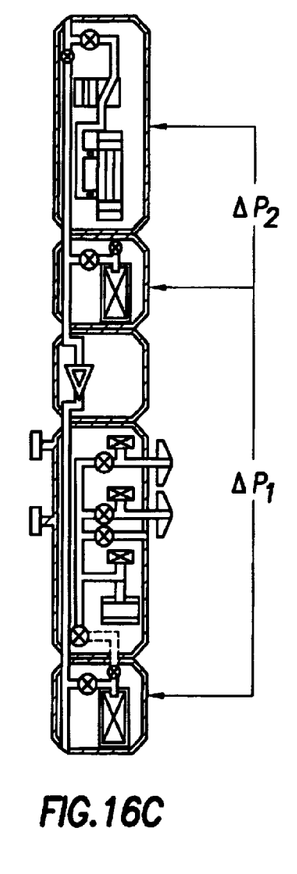

Referring now to FIGS. 16A, 16B, and 16C, there is illustrate the apparatus and method for determination of both density and viscosity.

EXAMPLES

The following examples are provided merely to illustrate the present invention, and are not intended to and do not limit the claims of the invention.

Example 1

This is a theoretical example. FIGS. 6 through 9 have detailed information on the prototype viscosity cell designs of the present invention. A leading taper is incorporated before the start of the shaped plug. This provides a continuous transition from the larger area in the annulus before the tapered cone section starts. This annulus area is considerably larger than the flow line (i.e., for the example shown, 0.11" radius) but the initial 15° taper transitions to the constant area profile desired at the start of the cone. From here the plug dimensions are governed by the following equations:
Constant area criteria:

$$r_{fl}^2 = r_o(x)^2 - r_i(x)^2 \quad \text{equal areas (sq. inches)}$$

$$\Delta x = \frac{r_o(0) - r_{fl}}{\tan(\theta)} \quad \text{offset length (inches)}$$

$$r_o(x) = r_{fl} + (x + \Delta x) \cdot \tan(\theta) \quad \text{tapered housing radius (inches)}$$

$$r_i(x) = \sqrt{(x + \Delta x) \cdot \tan(\theta)(2 r_{fl} + (x + \Delta x) \cdot \tan(\theta))} \quad \text{shaped plug radius function (inches)}$$

Given:
$r_{fl}$=0.11 RDT flow line radius (inches)
$r_o(0)$=0.1955 starting housing radius (inches)
L=8.0 taper length (inches)
$\theta$=6°/2=3° taper angle (degrees) Shaped plug calculations:

$$r_i(0) = \sqrt{r_o(0)^2 - r_{fl}^2} = 0.1616 \text{ starting plug radius (inches)}$$

$$\Delta x = \frac{r_o(0) - r_{fl}}{\tan(\theta)} = 1.6314 \text{ offset length (inches)}$$

$$r_o(8) = r_{fl} + (8 + \Delta x) \cdot \tan(\theta) = 0.6148 \text{ ending housing radius (inches)}$$

$$r_i(8) = \sqrt{(8 + \Delta x) \cdot \tan(\theta)(2 r_{fl} + (8 + \Delta x) \cdot \tan(\theta))} = 0.6048 \text{ ending plug radius (inches)}$$

To accommodate the additional 0.75 inches added to the plug the following housing dimensions need to be changed:

| Drawing | Dimension 1 | Dimension 2 |
| --- | --- | --- |
| 8" Long Housing | 1.75 changed to 2.5 | over all length increased by 0.75" |
| 5" Long Housing | 1.75 changed to 2.5 | over all length increased by 0.75" |

Example 2

Figure 10:
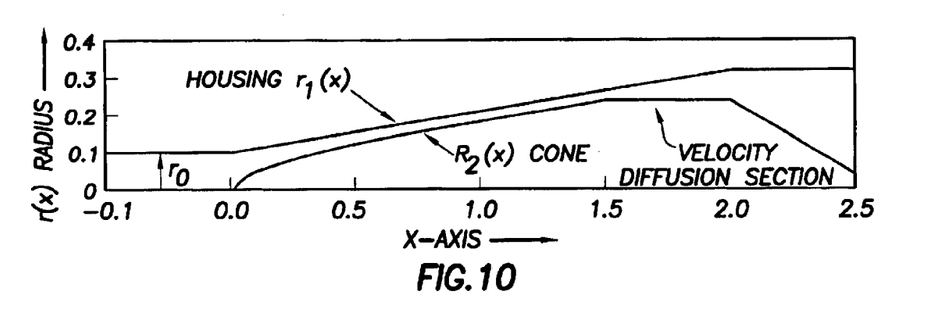
FIGS. 10 through 15 have detailed information on the prototype viscosity cell designs of Example 2.

This is a theoretical example. This example provide design calculations for the tapered cone housing (see FIG. 10) with shape functions for a constant area housing cone combination.

Figure 11:
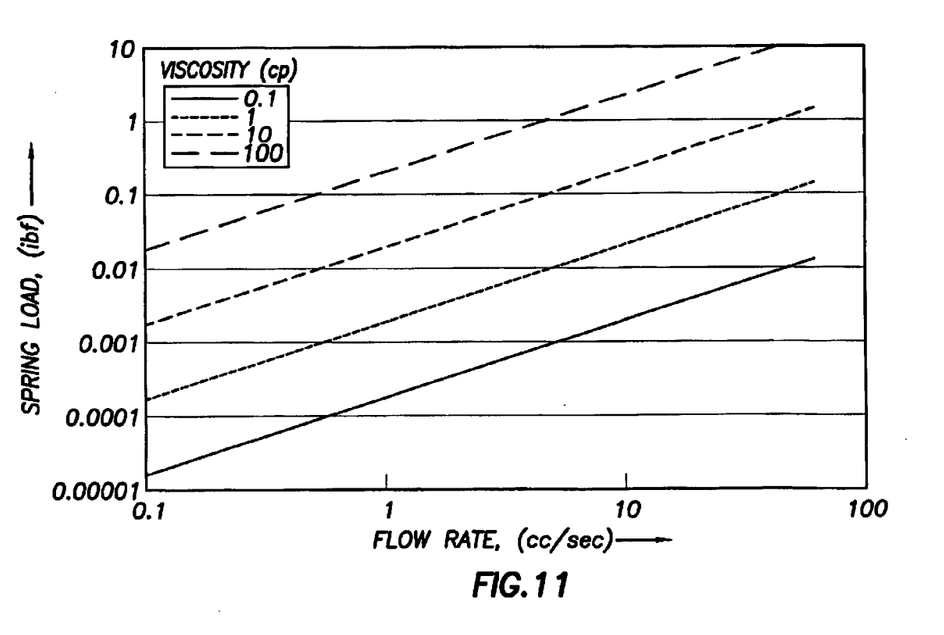

The estimated spring reaction load from the cone is shown in FIG. 11 and is based on the pressure drop across the cone and the maximum area of the cone.

Figure 6:
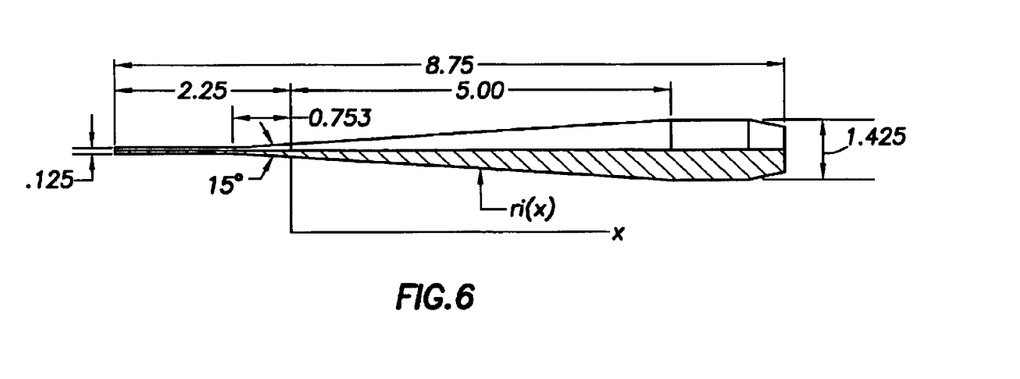
FIGS. 6 through 9 have detailed information on the prototype viscosity cell designs of Example 1.
Figure 7A:
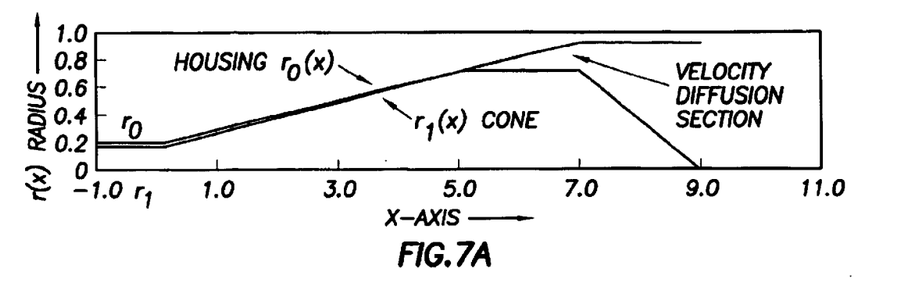
Figure 7B:
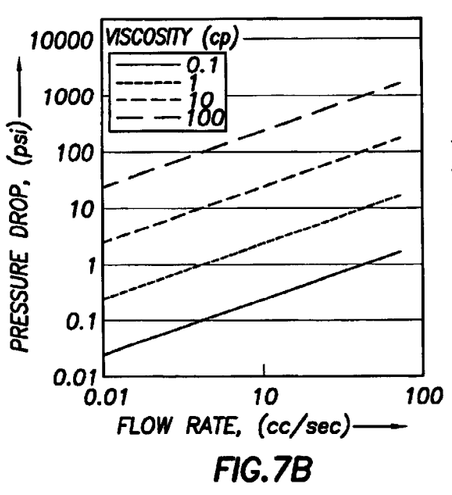
Figure 7C:
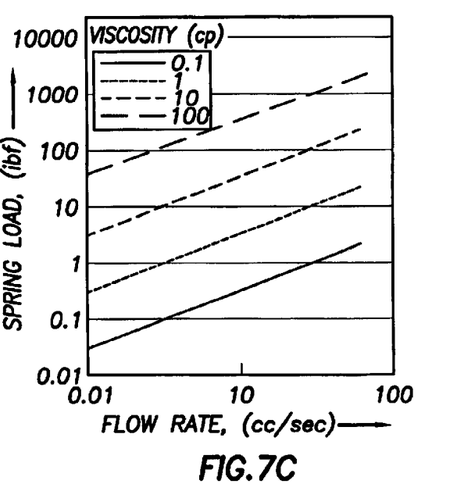
Figure 8:
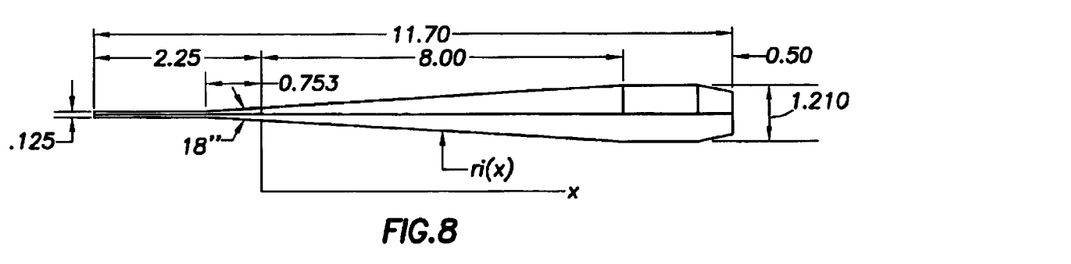
Figure 9A:
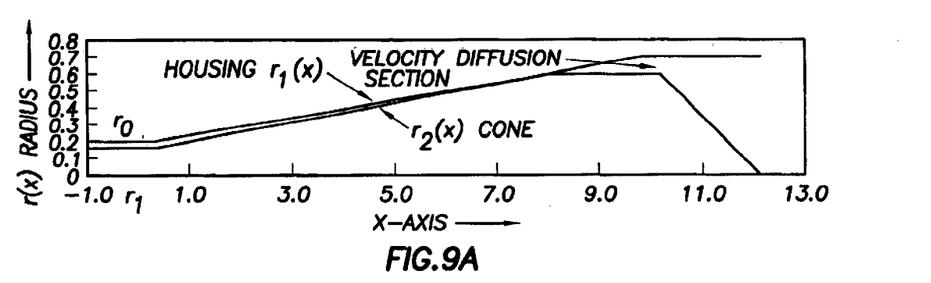
Figure 9B:
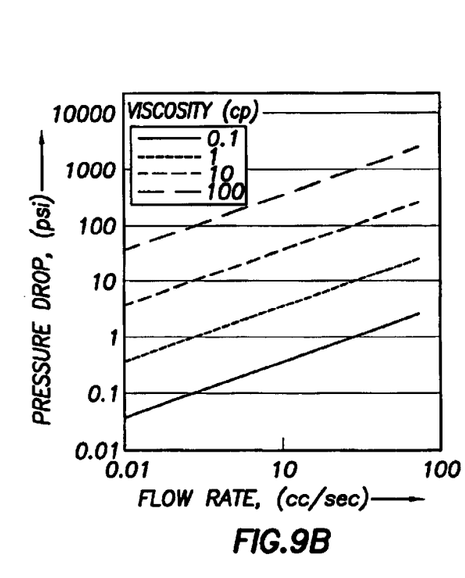
Figure 9C:
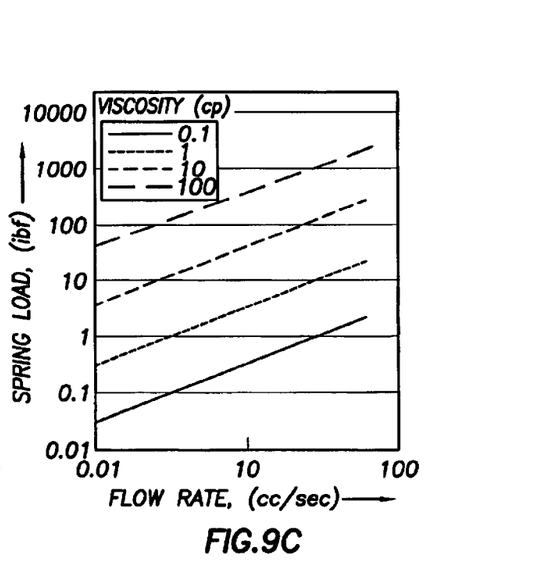
Figure 12:
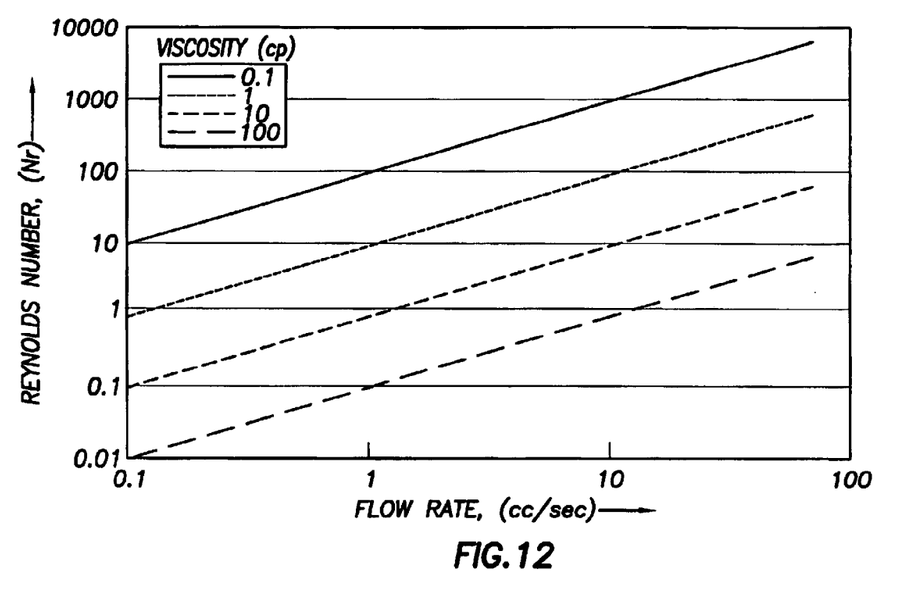
Figure 13:
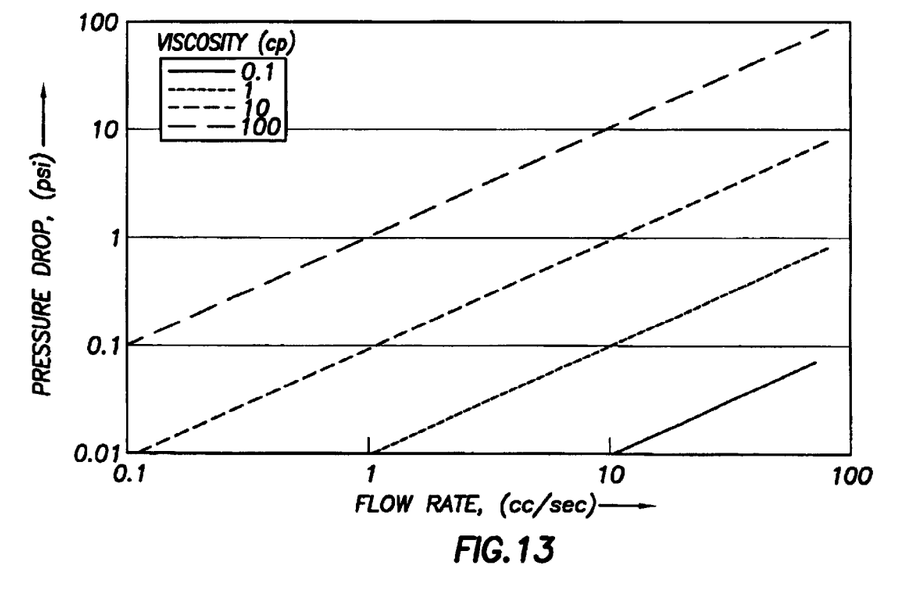
Figure 14:
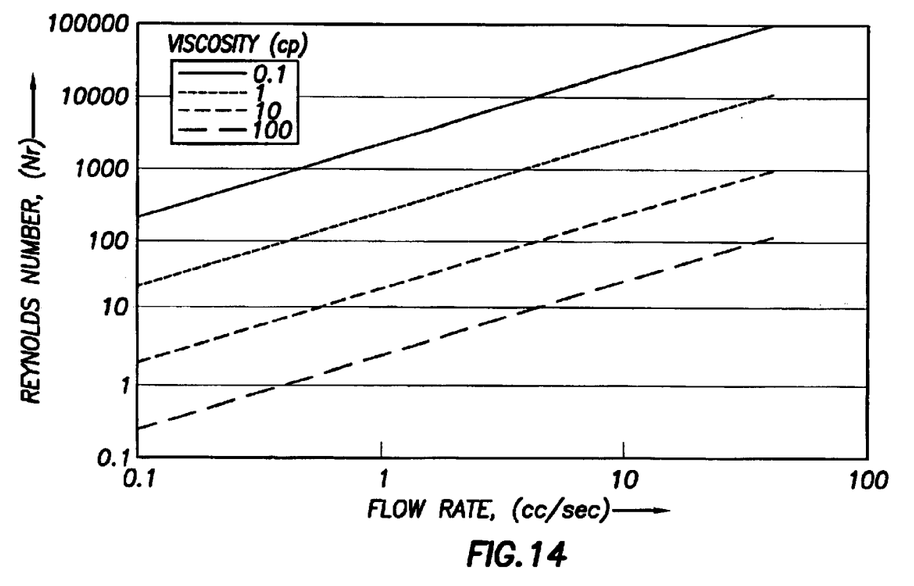
Figure 15:
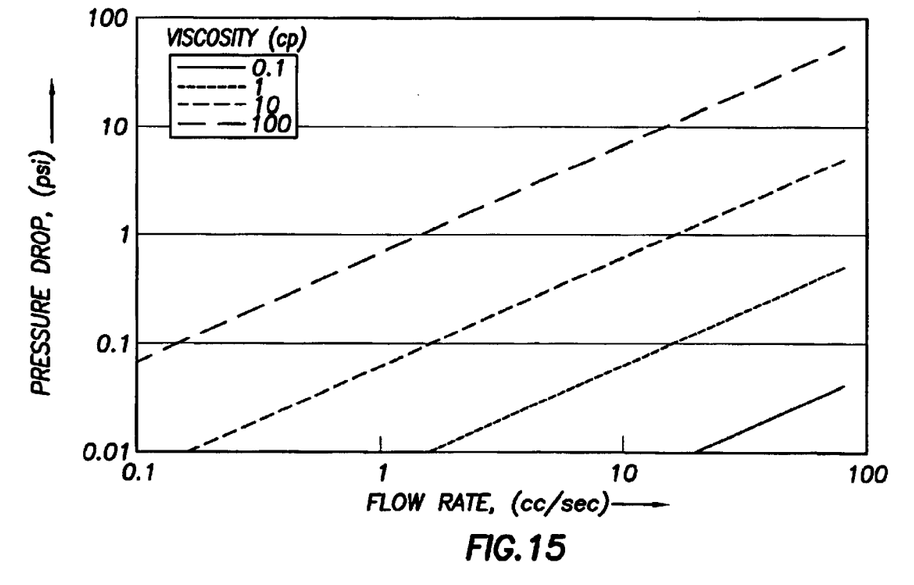

The Reynolds number of the flow through the cone and estimated pressure drop across the cone are shown in FIGS. 12 and 13 consecutively. The Reynolds numbers for the flow in the flow-line between the two quartz pressure gauges (4.2' apart) are shown in FIGS. 5 and 6 consecutively. It is interesting to note that while the Reynolds is reduced by more than an order of magnitude by the tapered cone, the estimated pressure drop through the cone is nearly equal to the flow line pressure drop. All estimates are made assuming laminar flow which should over estimate the pressure drop for cases where the flow is near transition or turbulent (i.e., $N_R$>2000).

The housing has a straight 6° taper and the inner cone is shaped according to the $r_2(x)$ functions developed below. This shape should minimize velocity variations entering the flow channel and provide a smooth transition to laminar flow. The velocity diffusion section is added to provide a smooth transition to the low velocity down stream region.

Given:
$r_o$=0.11 flow line radius (inches)
L=2.0 taper length (inches)
$\theta$=6° taper angle (degrees)
Constant area criteria:

$$r_o^2 = r_1^2 - r_2^2 \quad \text{equal areas (sq. inches)}$$

Shape functions:

$$r_1(x) = r_o + x \cdot \tan(\theta) \quad \text{tapered housing radius (inches)}$$

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled the art to which this invention pertains.

We claim:

1. A tool for processing a reservoir fluid in a subterranean well bore penetrating a reservoir, the tool comprising:
    (a) a housing suitable for insertion into the well bore, the housing defining a passage therethrough for providing fluid communication with the reservoir fluid, said passage having an entry region, an intermediate region, and an exit region,
        wherein for a fluid of a given viscosity at a given Reynolds number, the entry region has an entry region geometry that defines an entry region flow velocity, and the intermediate region has an intermediate region geometry that defines an intermediate region flow velocity, wherein the intermediate region flow velocity is not equal to the entry region flow velocity;
    (b) a pressure sensor for measuring a differential pressure across at least the intermediate region; and
        wherein a displaceable element is positioned in the passage, and the element is biased by a biasing device against force exerted on the element by fluid flow through the passage.

2. The tool of claim 1, wherein the intermediate region is self cleaning.

3. The tool of claim 1, wherein the pressure sensor measures pressure across the intermediate region.

4. The tool of claim 1, further comprising:
    (c) a flow meter for measuring the intermediate region flow velocity.

5. The tool of claim 4, further comprising:
    (d) a processor for determining physical characteristics of the fluid from at least one of the differential pressure and intermediate region flow velocity of the fluid.

6. The tool of claim 5, wherein the processor determines the viscosity of the fluid.

7. The tool of claim 1, further comprising,
    (c) a flow controller for controlling the intermediate region flow velocity of the fluid.

8. The tool of claim 7, further comprising:
    (d) a processor for determining physical characteristics of the fluid from at least one of the differential pressure and intermediate region flow velocity of the fluid.

9. The tool of claim 8, wherein the processor determines the viscosity of the fluid.

10. A method for processing a reservoir fluid in a subterranean well bore penetrating a reservoir, the method comprising the steps of:
    (a) passing the reservoir fluid through a passage having an entry region, an intermediate region, and an exit region, the fluid having a greater Reynolds number in the entry region than in the intermediate region, and a displaceable element positioned in the passage being biased by a biasing device against a force exerted on the element by fluid flow through the passage;
    (b) controlling a velocity of the fluid passing through the intermediate region; and
    (c) determining a differential pressure across at least the intermediate region.

11. The method of claim 10, further comprising determining a viscosity of the fluid from the velocity and differential pressure.

12. The method according to claim 10, further comprising the step of:
    (d) determining a differential pressure across a combination of the intermediate region and at least one of the entry and exit regions.

13. The method of claim 12, further comprising determining a viscosity and density of the fluid from the velocity and differential pressures.

* * * * *